United States Patent [19]

Rokos et al.

[11] Patent Number: 4,837,229
[45] Date of Patent: Jun. 6, 1989

[54] 5-AMINOSALICYLIC ACID-O-SULFATES OF PHYSIOLOGICALLY ACCEPTABLE BASES, PROCESS FOR THE PREPARATION THEREOF AND DRUGS CONTAINING SAME

[75] Inventors: Hartmut Rokos; Heinz Konczak, both of Berlin; Wolfgang Forth, Munich, all of Fed. Rep. of Germany

[73] Assignee: Henning Berlin GmbH Chemie- und Pharmawerk, Fed. Rep. of Germany

[21] Appl. No.: 224,238

[22] Filed: Jul. 25, 1988

Related U.S. Application Data

[63] Continuation of Ser. No. 47,518, May 6, 1987, abandoned, which is a continuation of Ser. No. 875,521, Jun. 19, 1986, abandoned, which is a continuation of Ser. No. 625,620, Jun. 28, 1984, abandoned.

[30] Foreign Application Priority Data

Jul. 1, 1983 [DE] Fed. Rep. of Germany ....... 3323702

[51] Int. Cl.$^4$ .................. A61K 31/38; C07C 71/00
[52] U.S. Cl. ........................ 514/517; 558/37
[58] Field of Search ............ 260/505 R; 558/37; 514/517

[56] References Cited

PUBLICATIONS

Chemical Abstracts Index 79 53744 (1973).
Engel, J. Amer. Chem. Soc., 51, 3483 (1929).

Primary Examiner—Alan Siegel
Attorney, Agent, or Firm—Wegner & Bretschneider

[57] ABSTRACT

5-Aminosalicylic acid O-sulfates of physiologically acceptable bases are new substances which are preparable by esterification of 5-nitrosalicylic acid alkyl esters with carbodiimide and sulfuric acid, alkaline saponification of the alkyl ester group and reduction of the thus obtained 5-nitrosalicylic acid O-sulfates. Said substances are useful as drugs, more specifically for the treatment of colitis ulcerosa, enteritis regionalis Crohn (morbus Crohn), chronic nonspecific colitis and diverticulitis.

16 Claims, No Drawings

5-AMINOSALICYLIC ACID-O-SULFATES OF PHYSIOLOGICALLY ACCEPTABLE BASES, PROCESS FOR THE PREPARATION THEREOF AND DRUGS CONTAINING SAME

This application is a continuation of U.S. application Ser. No. 047,518, filed May 6, 1987, now abandoned, which is a continuation of U.S. application Ser. No. 875,521, filed June 19, 1986, now abandoned, which is a continuation of U.S. application Ser. No. 625,620, filed June 28, 1984, now abandoned.

BACKGROUND OF THE INVENTION

The present invention relates to novel pharmacologically acceptable salts of 5-aminosalicylic acid O-sulfate, processes for the preparation thereof and drugs containing same which are suitable for the treatment of colitis ulcerosa, enteritis regionalis Crohn (morbus Crohn), chronic nonspecific colitis and diverticulitis.

The standard preparation for the treatment of said diseases has so far been salazosulfapyridine. Said compound has mostly been orally administered and is probably bacterially decomposed in the colon to give the two metabolites 5-aminosalicylic acid and sulfapyridine. The metabolite 5-aminosalicylic acid has appeared to be the active component while the frequently observed side-effects are to be attributed to the metabolite sulfapyridine; cf. Khan et al., Lancet 2, 892 (1977). As 5-aminosalicylic acid is instable and virtually cannot be conveyed into the colon via the oral route, there has already been contemplated by Khan, loc. cit., the possibility of synthesizing a new substance which does not exhibit said drawbacks inherent to the known salazosulfaypyridine.

From German Offenlegungsschrift (Published Unexamined Patent Application) No. 30 27 013 by applicants there has been known an agent for treating colitis ulcerosa, enteritis regionalis Crohn (morbus Crohn), chronic nonspecific colitis and diverticulitis, which agent contains salicylic azobenzoic acid. Said agent is being successfully tested under clinical conditions. However, the salicylic azobenzoic acid contains an azo moiety which is rated to be toxicologically doubtful and, hence, should be avoided in drugs if possible.

PRESENT INVENTION

Therefore, it is the object of the present invention to develop other derivatives of the 5-aminosalicylic acid which derivatives will evade the disadvantages of salazosulfapyridine and can be therapeutically used in at least a manner comparable to that of the salicylic azobenzoic acid.

The present inventors have now found that pharmacological acceptable salts of 5-aminosalicylic acid O-sulfate are excellently suitable to serve said purpose and, in addition, have the advantage that they release the desired 5-aminosalicylic acid in the colon more uniformly and over an extended period of time.

5-aminosalicylic acid O-sulfate and pharmalogically acceptable salts thereof have so far not been described in the literature. Although there is apparent from the index of Chemical Abstracts that "Benzoic Acid, -5-amino-2-sulfooxy-" have already been described, in Chemical Abstracts 79, 53744 (1973) there has been only been referred to German Offenlegungsschrift 21 56 556 wherein unambiquously there has only been described the 5-amino-3-sulfosalicylate of nucleotide amino acid products. The 5-aminosulfosalicylic acid is a sulfonic acid which is formed by sulfonation of aminosalicylic acid. In contrast, the 5-aminosalicylic acid O-sulfate of the present invention is not a sulfonic acid but is a sulfuric acid ester of the phenolic OH group of the aminosalicylic acid. Said sulfuric acid esters so far have not been preparable by way of a direct synthesis.

In a paper by Engel on the cleavage of azo dyes by means of sulfites (J.Amer.Chem.Soc. 51, 3483 (1929) there is described a supposed preparation of 5-aminosalicylic acid O-sulfuric acid ester. However, this reported result must have been an obvious misinterpretation of experimental results, for the properties of the product then found are in no way in agreement with the those of the real 5-aminosalicylic acid O-sulfuric acid ester or of the 5-aminosalicylic acid O-sulfates according to the invention. Among other findings, the substance as described in said reference was stable against strong acids and was only decomposed to a slight extent upon boiling in a 5 mol/l hydrochloric acid for an extended period of time. Also, the experiments aiming towards a direct preparation of a 5-aminosalicylic acid O-sulfuric acid ester are not consistent with the possibility that at that time said substance would have been formed and recovered at all.

According to the present invention, 5-aminosalicylic acid O-sulfate can be prepared by esterification of 5-nitrosalicylic acid alkyl esters with carbodiimide and sulfuric acid, alkaline saponification of the alkyl ester group and reduction of the thus obtained 5-nitrosalicylic acid O-sulfate.

All lower alkyl esters may be considered as alkyl esters to be employed. The ethyl ester known from the literature is preferably used; cf. P. Thieme, J. für prakt. Chem. 43, 453 (1891). However, the methyl ester, propyl ester or butyl ester may be used in the same way.

The esterification of the phenolic OH group according to the invention is effected by reaction with carbodiimides and sulfuric acid. All of the conventional carbodiimides suitable for the esterification can be used. Dicyclohexylcarbodiimide is preferably used. In the next steps, in an optional sequence, the alkyl ester group is saponified under alkaline conditions, and the 5-nitro group is reduced to yield a 5-amino group. The saponification of the alkyl ester group must be carried out under alkaline conditions, since the sulfuric acid esters of the phenol group are extremely sensitive to acids (sensitivity towards acids is so strong that free 5-aminosalicylic acid O-sulfuric acid decomposes within a short time). The reduction of the 5-nitro group to form a 5-amino group is effected in a per se known manner, in a particularly simple manner by catalytic hydrogenation under regular pressure or elevated pressure.

Depending on by which base the alkaline saponification is effected there is directly obtained the corresponding salt of the 5-aminosalicylic acid O-sulfuric acid ester. With view to the crystallizability thereof and, hence, the easy purification of the dipotassium salt, potassium hydroxide solution is preferred to be used as the base. However, other suitable bases such as sodium hydroxide may be employed.

The conversion of the dipotassium salt into other pharmacologically acceptable salts is accomplished in a per se known manner, for example by means of appropriately charged ion exchangers, by reaction with a solution containing a pharmacologically acceptable cation which forms a less soluble salt than the dipotassium salt, etc.

The pharmacologically acceptable salts of 5-aminosalicylic acid O-sulfate have the surprising property that they do not undergo any substantial decomposition in the small intestine. They, however, are slowly and uniformly decomposed in the large intestine/colon, probably by the action of the bacteria and enzymes as present therein, to form the desired 5-aminosalicylic acid and the physiologically acceptable sulfates. Thus, the substances according to the invention in an ideal manner allow the 5-aminosalicylic acid to be conveyed to the site of its desired efficacy.

Accordingly, the present invention further relates to pharmaceutical compositions containing pharmacologically acceptable salts of 5-aminosalicylic acid O-sulfate. It was certainly not foreseeable that such relatively low molecular weight salts of sulfuric acid esters are not substantially resorbed in the small intestine whereas they are decomposed in the desired manner so as to become available in the large intestine.

The salts according to the invention may be employed in the forms of tablets, dragees, but also as enemae. Since the decomposition is to occur only in the large intestine or colon or the rectum, the tablets or dragees according to invention are preferably soluble in the small intestine. To this end, for example, a recipe is selected in which the substances will only be dissolved in the alkaline medium of the small intestine. However, said goal is more readily achieved by coating the tablets or dragees with a known per se enteric coating such as that preparable by use of the Eudragit varnishes available from the company of Röhm, which film is soluble in the small intestine.

In the preparation of pharmaceuticals according to the invention all conventional excipients and auxiliary agents for the preparation of tablets and dragees maybe used. Said excipients and auxiliary agents include talc, starch, cellulose, polyvinlypyrrolidone, magnesium stearate etc.. More specifically, for the preparation of formulations soluble in the small intestine there are suitable polycarboxylic acids and and other polymers which are only decomposed or dissolved in an alkaline medium. The conventional coatings soluble in the small intestine do also mostly consist of such acidic polymers which are only decomposed or dissolved in an alkaline medium.

The cation portion of the salts of the present invention does not play a crucial role with respect to the activity and resorption. Thus, instead of potassium as already mentioned above, sodium, ammonium, calcium, magnesium, and the like may be used. Also salts of physiologically acceptable amines may be also employed in practice. Dibasic salts are preferred.

The tablets or dragees according to the invention generally contain from 0.3 to 1 g of pharmacologically acceptable 5-aminosalicylic acid O-sulfate salt. For the treatment of acute inflammatory processes, adults are orally administered a daily dose of from 1 to 6 g of the active ingredient. For relapse prophylaxis inpermanent therapy, 1 to 4 g distributed over the dayinto several individual doses will be sufficient. Since the side-effects as previously observed in the therapy with salazosulfapyridine have not been observed upon use of the agents according to the invention, the dosages may also be increased over those having so far been administered.

Therapy usually utilizes the oral route, while tablets or film dragees which are soluble in the small intestine are preferred to be used. Under particular circumstances, more specifically in the case that the residence time in the intestine is strongly reduced, there may also be used stomach-soluble tablets or dragees.

More particularly, in cases of a stationary treatment the utilization of enemae is also to be taken into consideration, in which treatment up to 100 ml of enema may be introduced once or several times a day. Such an enema preferably should contain 1 to 6 g, preferably 3 g, of 5-aminosalicylic acid O-sulfate salt in 100 ml solution. Enemae having been prepared in advance, thus, should contain from 10 to 60 g/l, preferably 30 g/l, of the active ingredient.

The following examples illustrate the preparation and effectiveness of pharmacologically acceptable salts of 5-aminosalicylic acid O-sulfate according to the invention.

EXAMPLE 1

With cooling by means of an ice bath, a cold solution of 10.14 g of 5-nitrosalicylic acid ethyl ester (P. Thieme, Journal f. prakt. Chem. 43, 453 (1891) in 60 ml of dimethylformamide (DMF) is added to a stirred solution of 74.26 g N,N'dicyclohexylcarbodiimide (DCC) in 80 ml of DMF. Then 3.8 ml of concentrated sulfuric acid in 60 ml DMF are added. The suspension is stirred in an ice bath for 1 hour and subsequently at room temperature for 22 hours.

After cooling in an ice bath, a cold solution of 6.75 g $K_2CO_3$ (anhydrous) in 50 ml of water is added. The thus obtained mixture is added to 2.4 l of stirred ice water. After allowing to sit in the ice bath for 75 minutes, the filtrate is separated from the precipitated dicyclohexyl urea. The filter residue is washed twice with 150 ml of water each. The yellow filtrate is concentrated to form a syrup; the latter crystallizes upon addition of 1,500 ml of diethyl ether and 60 ml of ethanol. Once the crystallization is completed, the product is separated by suction-filtration, then several times washed with diethyl ether and dried in a desiccator.

Yield: 16.7 g 5-nitrosalicylic acid ethyl ester O-sulfate (potasium salt).

Thin layer chromatography (TLC): Silicagel; isopropanol/chloroform/methanol/water (37/37/19/7;v/v); $R_f=0.74$.

16.7 g of 5-nitrosalicylic acid ethyl ester O-sulfate (potassium salt) are dissolved in 790 ml of diluted potassium hydroxide solution (4.4 g of KOH) and allowed to stand at room temperature for saponification.

Then, diluted acetic acid is slowly added to the stirred mixture until a pH of 8 is reached. After the addition of 820 ml of water and 3.16 g of a Pd catalyst (10% on $BaSO_4$, Degussa type E 50 N), hydrogen is passed through the mixture (a pressure vessel may be employed in order to accelerate the reduction).

Upon completion of the reduction (TLC; cf. above), the catalyst is filtered off by suction filtration, and the filtrate is concentrated to 90 ml. Then, 390 ml of anhydrous ethanol are added to the stirred concentrate. Upon completion of the crystallization, the product is filter off with suction, washed and dried in a desiccator.

Yield: 9.9 g 5-aminosalicylic acid O-sulfate (di-potassium salt).

Thin layer chromatography (TLC): Silicagel; isopropanol/chloroform/methanol/water (37/37/19/7;v/v); $R_f=0.0$.

The decomposition of the sulfuric acid ester with 2 N hydrochloric acid at 110° C. or with aryl sulfatase (EC 3.1.6.1) (Boehringer Mannheim) yielded 5-aminosalicylic acid (TLC in the above system; $R_f=0.38$).

Prior to analysis, the product was once more precipitated from an aqueous solution by addition of ethanol. Colorless crystals; m.p. in excess of 280° C.

Elementary analysis: $C_7H_5K_2NO_6S \cdot H_2O$ (327.4)

|  | C | H | K | N | S |
|---|---|---|---|---|---|
| Calc.: | 25.7 | 2.2 | 23.9 | 4.3 | 9.8% |
| Found: | 25.6 | 2.1 | 23.8 | 4.2 | 9.8%. |

EXAMPLE 2

Resorption of 5-aminosalicylic acid O-sulfate dipotassium salt (ASA-S) in comparison with 5-aminosalicylic acid (ASA) and salicylic azobenzoic acid (HB-313).

The respective resorptions were tested in the small intestine of rats (2 to 5 animals each). ASA and ASA-S were assayed by HPLC and fluorescence detector:

Column: RP-18 (5 μm); 120 mm×4.6 mm;
Eluant: acetonitrile/0.2 M phosphate, pH 7.5/1.25 mM cetyltrimethyl-ammoniumbromide (30/5/65; v/v/v/);
Flow: 1 ml/min;
Detector: fluorescence, 315/500 nm.

|  | μg/ml | % |
|---|---|---|
| ASA | | |
| Initial Value | 5.41 | 100 |
| After 20 min | 4.87 ± 0.39 | 90.0 |
| After 40 min | 4.26 ± 0.76 | 78.7 |
| After 60 min | 3.12 ± 0.39 | 57.7 |
| ASA-S | | |
| Initial value | 10.93 | 100 |
| After 20 min | 10.65 ± 1.60 | 97.4 |
| After 40 min | 12.13 ± 1.05 | 110.9 |
| After 60 min | 10.37 ± 0.91 | 94.9 |

2 ml of the dioxane solution were extracted with isoamyl acetate, re-extracted with sodium hydroxide solution and measured at 448 nm:

| HB-313 | μg/ml | % |
|---|---|---|
| Initial value | 8.72 | 100 |
| After 20 min | 8.75 ± 1.21 | 100.3 |
| After 40 min | 8.58 ± 0.95 | 98.4 |
| After 60 min | 9.00 ± 0.86 | 103.2 |

EXAMPLE 3

Resorption and Decomposition in a Voluntary Test Person.

|  | ASA-S | HB-313 |
|---|---|---|
| Active Ingredient | | |
| Single Dose | 2.74 | 300 |
| corresponding to ASA (g) | (1.36) | (1.60) |
| Ac-ASA Serum Level (μg/ml) | | |
| 6 h | 1.10 | 0.12 |
| 8 h | 0.97 | 0.46 |
| 12 h | 0.52 | 0.98 |
| 24 h | — | 0.65 |
| 25 h | 0.50 | — | after administration.
Ac-ASA Accumulated Urine Excretion (% of Dose)

| 24 h | 4.91 | 9.17 |
|---|---|---|
| 48 h | 8.16 | 10.02 | after administration.

Abbreviations:

| ASA | 5-aminosalicylic acid; |
|---|---|
| ASA-S | 5-aminosalicylic acid O—sulfate; |
| Ac-ASA | N—acetyl-5-aminosalicylic acid; |
| HB-313 | salicylic azobenzoic acid. |

The above results show that ASA-S, in the same manner as HB-313, is substantially not resorbed in the small intestine, while, however, it then releases ASA in the large intestine uniformly and over a longer period of time than HB-313 does, the ASA being resorbed and excreted via urine. No side effects were observed with the test person.

What is claimed is:

1. A pharmacologically acceptable salt of 5-aminosalicylic acid O-sulfate.
2. A salt according to claim 1 which is dibasic.
3. The salt according to claim 2 which is dipotassium 5-aminosalicylic acid O-sulfate.
4. A process for preparing salts of 5-aminosalicylic acid O-sulfate, which comprises esterifying 5-nitrosalicylic acid alkyl ester with a carbodiimide and sulfuric acid, hydrolyzing the resultant alkyl ester moiety under alkaline conditions, and reducing the thus obtained 5-nitrosalicylic acid O-sulfate.
5. The process according to claim 4, wherein the alkyl ester is the ethyl ester.
6. The process according to claim 4, wherein the carbodiimide is dicyclohexyl carbodiimide.
7. The process according to claim 4, wherein the hydrolysis under alkaline conditions is carried out by using a potassium hydroxide solution.
8. A pharmaceutical composition for treating inflammatory bowel disease comprising an effective amount of a pharmacologically acceptable salt of 5-aminosalicylic acid O-sulfate, and a pharmacologically acceptable carrier therefor.
9. The composition according to claim 8 wherein the salt is dipotassium 5-aminosalicylic acid O-sulfate.
10. A method for the treatment of inflammation of the intestines which comprises administering a therapeutically effective amount of a compound of claim 1.
11. A method for the treatment of inflammation of the colon which comprises administering a therapeutically effective amount of a compound of claim 1.
12. A method for making 5-nitrosalicylic acid alkyl ester O-sulfate comprising esterifying 5-nitrosalicylic acid alkyl ester with a carbodiimide and sulfuric acid.
13. The method of claim 12, wherein the alkyl ester is ethyl ester.
14. The method of claim 12, wherein the carbodiimide is dicyclohexyl carbodiimide.
15. The method of claim 12 further comprising hydrolyzing 5-nitrosalicylic acid alkyl ester O-sulfate under alkaline conditions to obtain 5-nitrosalicylic acid O-sulfate.
16. The method of claim 15 wherein hydrolyzing under alkaline conditions is carried out using a potassium hydroxide solution.

* * * * *